United States Patent [19]

Kamienski et al.

[11] Patent Number: 5,208,072

[45] Date of Patent: May 4, 1993

[54] MASS TREATMENT OF CELLULOSIC MATERIALS

[75] Inventors: Conrad W. Kamienski; Robert S. Wedinger, both of Gastonia, N.C.

[73] Assignee: FMC Corporation, Philadelphia, Pa.

[21] Appl. No.: 792,499

[22] Filed: Nov. 13, 1991

Related U.S. Application Data

[60] Division of Ser. No. 630,721, Dec. 20, 1990, Pat. No. 5,104,997, and a continuation of Ser. No. 252,421, Sep. 30, 1988, abandoned.

[51] Int. Cl.$^5$ .................. B05D 1/18; B05D 3/00
[52] U.S. Cl. ...................... 427/296; 427/439
[58] Field of Search ............ 162/9, 157.6, 158, 168.1, 162/181.1, 181.2, 182; 427/296, 439

[56] References Cited

U.S. PATENT DOCUMENTS

| | | | |
|---|---|---|---|
| 3,472,611 | 10/1969 | Langwell | 21/58 |
| 3,676,182 | 7/1972 | Smith | 117/60 |
| 3,703,353 | 11/1972 | Kusterer et al. | 21/58 |
| 3,778,401 | 12/1973 | Hayworth | 260/29.6 |
| 3,837,804 | 9/1974 | Walker et al. | 21/58 |
| 3,939,091 | 2/1976 | Kelly | 252/189 |
| 3,969,549 | 7/1976 | Willams et al. | 427/248 |
| 4,051,276 | 9/1977 | Williams et al. | 427/248 |
| 4,318,963 | 3/1982 | Smith | 428/537 |
| 4,522,843 | 6/1985 | Kundrot | 427/27 |
| 4,860,685 | 8/1989 | Smith | 427/140 X |
| 5,094,888 | 3/1992 | Kamianski et al. | 427/419.8 X |

FOREIGN PATENT DOCUMENTS 911110 10/1972 Canada .

OTHER PUBLICATIONS

Library of Congress Information Bulletin vol. 41, No. 15 Library Licensed to Make Deacidification Solution by Wei T'O Associates, Inc.

Mass Deacidification for Libraries, by George Martin Cunha, Library Technology Reports, May-Jun. 1987, vol. 23, No. 3.

*Primary Examiner*—Michael Lusigan
*Attorney, Agent, or Firm*—C. C. Fellows; R. L. Andersen; C. W. Kamienski

[57] ABSTRACT

This invention provides a process for deacidifying paper by contacting the paper with hydrocarbon or halocarbon solutions of certain magnesium and/or zinc alkoxyalkoxides which may have been treated with carbon dioxide to yield low viscosity solutions.

19 Claims, No Drawings

MASS TREATMENT OF CELLULOSIC MATERIALS

This application is a division of U.S. patent application Ser. No. 630,721 filed Dec. 20, 1990, now U.S. Pat. No. 5,104,997, patented Apr. 14, 1992, application was a Rule 62 and a continuation of U.S. application Ser. No. 252,421, filed Sep. 30, 1988, now abandoned.

This invention concerns a method for treating cellulosic materials such as paper by neutralizing the acidity of the paper and buffering the paper to the alkaline side to provide protection of the paper from post-treatment acid attack and to improve paper performance and novel chemical compositions useful in practicing this method of paper treatment.

Paper has been made for nearly 2,000 years; some early papers have lasted half of this time and others made during the middle ages are in excellent condition. Ancient handmade paper was too soft a material for receiving ink so it was sized by dipping the sheets in hot animal gelatin or starch. As papermakers shifted to machine made paper, different procedures for sizing the paper were necessary. This problem was solved by "tub sizing," which is done by adding a mixture of alum and rosin to the wet fiber slurry before the sheet was formed on the machine, thereby coating the fibers in the paper with rosin and making the paper suitable for use in printing paper or writing paper. Unfortunately, alum, aluminum sulfate $[Al_2(SO_4)_3]$, which is used in tub sizing to uniformly distribute the rosin throughout the sheet is one of the major causes of acid in paper. Subsequent reaction between aluminum sulfate and water produces sulfuric acid. Other sources of acid in the paper, of course, include industrial atmospheres that have sulfur dioxide and nitrogen oxides in the air which form acid in the paper. Thus, most books printed in the last 100 or 150 years were printed on acid paper which becomes brittle and disintegrates in a period of 5-75 years or more depending on the care with which books have been stored.

Almost every library in the world is filled with books made with this acid paper, and therefore, have large collections of books which are disintegrating. This problem of acidity in books has been recognized for quite a long time and a great deal of work has been done to establish a process for deacidifying such books. A recent report, "Mass Deacidification for Libraries" by George Martin Cunha, Adjunct Professor of Conservation, College of Library and Information Science, University of Kentucky, was printed in Library Technology Reports, Volume 23, No. 3, May-June, 1987. The Cunha report claims to have reviewed all known experiments with methods of mass deacidification and six were thoroughly investigated. One of the major methods of mass deacidification considered was the so-called diethyl zinc (DEZ) system which appears to be covered by U.S. Pat. Nos. 3,969,459 and 4,051,276 assigned to the United States of America as represented by the Librarian of Congress. Mass deacidification with diethyl zinc is a 50-55 hour three-phase process consisting of preconditioning, permeation and passivation. The DEZ system under development by the Library of Congress will handle thousands of books per cycle. However, liquid diethyl zinc is pyrophoric (will spontaneously ignite when exposed to air) and will react explosively with water. The fire and explosive hazards of diethyl zinc make it a dangerous chemical to work with and probably one that every library could not contemplate using. Moreover, the fire and explosive hazards have caused considerable expensive design problems in developing suitable equipment for this process.

Another major method of mass deacidification evaluated in the Cunha report was one employing methoxymagnesium methylcarbonate in a solution of alcohol and fluorocarbons in treating books in mass. The system is a liquid process designed to dissolve, transport and deposit the chemicals into book pages to neutralize acids present in the paper and to deposit buffering chemicals that will neutralize any acids that may subsequently contaminate the paper. This system appears to be covered by U.S. Pat. No. 4,318,963 of Richard D. Smith and U.S. Pat. No. 3,939,091 of George B. Kelly (assigned to the United States of America as represented by the Librarian of Congress) and is based on earlier U.S. Pat. Nos. 3,676,055 and 3,676,182 to Richard D. Smith. The process employs methoxymagnesiummethyl carbonate dissolved in a liquid solution of fluorocarbons and methyl alcohol. This alcohol is necessary to promote solution of the magnesium compound. This solution reacts with water in the paper to form magnesium carbonate, magnesium hydroxide and magnesium oxide, some of which react with the acid in the paper to form neutralized salts. The remaining mixture of carbonate, hydroxide and oxide remains in the paper as basic magnesium carbonate which forms an alkaline reserve or buffering agent that will neutralize future acid contamination of the paper. Disadvantages of the process include feathering of alcohol-soluble inks and colors and attack on some highly nitrated book covers, and thus a pre-sorting by uses is required.

According to the Cunha report, ammonia has been used in India for mass deacidification of books. Langwell in England used cyclohexylamine carbonate, while in the United States the Barrow Laboratory in Virginia conceived the use of morpholine (U.S. Pat. No. 3,771,958). The morpholine, ammonia and cyclohexylamine carbonate systems were moderately effective deacidifiers, but did not provide a buffer in the paper to provide protection of the paper from post-treatment acid attack. A patent to R.A. Kundrot (U.S. Pat. No. 4,522,843) claims a method of deacidifying books using alkaline particles of a basic metal suspended in an aerosol.

The present invention provides a process in which certain carbonated magnesium alkoxyalkoxides can be readily prepared and dissolved in a wide variety of solvents both liquid and gaseous at ordinary temperatures and said solutions applied to paper, books, and other cellulosic materials to both deacidify, coat them in a protective manner, and to provide them with added strength.

SUMMARY OF THE INVENTION

In accordance with this invention, there is provided a process for deacidifying paper using certain magnesium and zinc alkoxyalkoxides, described in U.S. Pat. No. 4,634,786, cols. 7-10 and 17, and dissolved in hydrocarbon or halocarbon solvents, which are treated with gaseous carbon dioxide to, unexpectedly, yield solutions possessing a much reduced viscosity. These solutions can be readily solvent-stripped to yield fluid, somewhat viscous liquid residues, which readily redissolve in a variety of gaseous and liquid hydrocarbon and halocarbon solvents to yield highly concentrated, low viscosity solutions, which can be adjusted in concentration to that needed for treatment of books and paper. Optionally an aluminum or zinc alkoxide can be added to these carbonated alkoxide compositions to help solubilize the components of the compositions.

Examination of the resulting carbonated magnesium-containing residues, or solutions thereof, show that approximately 50% of the magnesium alkoxyalkoxide groupings have been converted to magnesium alkoxyalkyl carbonate groupings.

These carbonated magnesium alkoxyalkoxides (or magnesium alkoxyalkyl carbonates) either in a neat form or in a solution form, can be treated with gases, such as gaseous hydrocarbons, for example ethane or carbon dioxide, under relatively low pressure, to yield greatly expanded solutions of the magnesium-containing product. Thus, for example, treatment of a 5-10 weight percent solution of magnesium n-hexylcarbitolate (carbonated) in hexane with sufficient ethane gas to raise the pressure to about 500 psi causes the liquid volume of the solution to increase to approximately twice its original volume.

The above property of volume expandability can be utilized to alternately cover and uncover paper products suspended in the same chamber. Thus, a strip of paper cut from a book, when suspended vertically above the original carbonated magnesium n-hexylcarbitolate solution in hexane, is contacted by the solution to a point more than halfway to the top of the paper strip, by pressurizing the magnesium-containing solution with ethane as described above. Release of the pressure and venting of the gas returns the liquid solution to its original volume below the bottom edge of the paper strip.

Said paper strip is now treated evenly with the magnesium-containing compound and possesses a satiny feel.

Unlike magnesium alkoxide carbonates described in the literature, such as methoxymagnesium methyl carbonate no alcohol co-solvent is required to maintain the solubility of the carbonated magnesium alkoxides of this invention either in hydrocarbon or halocarbon solution. Alcohol co-solvents have been shown to be detrimental in book deacidification, dissolving inks and colors and attacking plastic covers in the books.

In addition, other metallic alkoxides (such as aluminum alkoxides) based on alcohols described in U.S. Pat. No. 4,634,786, cols. 7-10, and 17 can be prepared in liquid form and dissolved in a variety of solvents, including hydrocarbons and halocarbons. The corresponding aluminum alkoxides can be readily prepared and combined with the carbonated magnesium and/or zinc alkoxides of this invention and dissolved in a variety of solvents to yield solutions which can be gas expanded or used directly in the treatment of paper and books.

Thus, it is one advantage of this invention to make available carbonated magnesium alkoxides possessing a high solubility in liquid hydrocarbon and halocarbon solvents, said solutions also having the property of low viscosity.

It is another advantage of this invention to provide a process for greatly expanding the volume of these solutions of carbonated magnesium alkoxides without causing the separation of carbonated magnesium alkoxides from these solutions.

It is another advantage of this invention to provide a simplified process for the utilization of such expanded solutions of carbonated magnesium alkoxide in the treatment of paper, books, and other cellulosic materials, whereby the latter are deacidified, buffered, and given a permanent finish by these expanded solutions.

It is another advantage of this invention to provide a simplified process for the utilization of solutions of carbonated magnesium alkoxide, per se, in the treatment of paper, books, and other cellulosic materials whereby the latter are deacidified, buffered and strengthened by these solutions.

It is yet another advantage of this invention to provide such deacidifying carbonated magnesium alkoxide solutions in the essential absence of co-solvent alcohols.

It is also an advantage of this invention to provide other low viscosity metallic alkoxides solutions for use as deacidifying solutions in liquid or gaseous hydrocarbon and halocarbon solvents, such as, for example aluminum alkoxides, alone or in combination with the carbonated magnesium and zinc alkoxides of this invention.

A process for deacidifying paper, books and other cellulosic materials, according to this invention comprising contacting the cellulosic materials with an effective amount of a composition selected from the group consisting of: (A) a substituted metal alkoxide having the formula

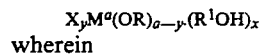

wherein
(I) —OR is a group selected from 2-alkoxyalkoxy- and 1-alkoxypolyalkoxy- groups of the formula

wherein $R^2$ is selected from H and —$CH_3$ and $R^3$ is selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20;

(II) X- is a group selected from (a) 2-dialkylaminoalkoxy- and α-dialkylaminopolyalkoxy groups of the formula

wherein $R^2$ is selected from hydrogen and methyl, $R^3$ is selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20;

(b) a halogen selected from chlorine and bromine;

(c) an organic group —$R^4$ wherein $R^4$ is selected from the group consisting of alkyl groups containing 1 to 18 carbon atoms, cycloalkyl groups containing 3 to 18 carbon atoms and aryl, arylalkyl and alkylaryl groups containing 6 to 18 carbon atoms;

(d) an acyloxy group of the formula [—O(O)$CR^4$] wherein $R^4$ has the hereintobefore ascribed meaning;

(e) ω-alkoxypolyalkoxy- groups of the formula

wherein $R^2$, $R^3$ and n have the hereintobefore ascribed meanings;

(f) an alkoxy group —$OR^4$ wherein $R^4$ has the hereintobefore ascribed meanings;

(III) M is a metal selected from groups IIa and IIb of the Periodic Table and aluminum and mixtures thereof;

(IV) $R^1OH$ is a compound in which $R^1O$ is a group selected from (e) alkoxy groups of the formula $R^4O$ wherein $R^4$ has the hereintobefore ascribed meanings;

(f) 2-alkoxyalkoxy- and ω-alkoxypolyalkoxy- groups of the formula

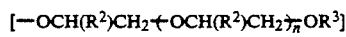
$[-OCH(R^2)CH_2+OCH(R^2)CH_2\overline{)_n}OR^3]$ wherein $R^2$, $R^3$ and n have the hereintobefore ascribed meanings;

(g) 2-dialkylaminoalkoxy- and ω-dialkylaminopolyalkoxy groups of the formula

$[-OCH(R^2)CH_2+OCH(R^2)CH_2\overline{)_n}NR_2^3]$ (V) a is the valence of the metal M;
(VI) y has a value between zero and one; and
(VII) x has a value of zero to two;
(B) a carbonated substituted metal alkoxide having the formula $X_yM^a(OR)_{a-y}(R^1OH)_x$ in which either $X_y$ or —OR is carbonated wherein $R^1OH$, M, a, y and x have the hereintobefore ascribed meanings; and (I) —OR is a group selected from 2-alkoxyalkoxy- and ω-alkoxypolyalkoxy- groups of the formula

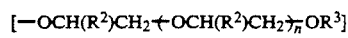
$[-OCH(R^2)CH_2+OCH(R^2)CH_2\overline{)_n}OR^3]$ wherein $R^2$ is selected from H and —$CH_3$ and $R^3$ is selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20; and (II) X— is a group selected from (a) 2-dialkylaminoalkoxy- and ω-dialkylaminopolyalkoxy groups of the formula

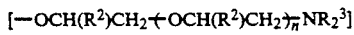
$[-OCH(R^2)CH_2+OCH(R^2)CH_2\overline{)_n}NR_2^3]$ wherein $R^2$ is selected from hydrogen and methyl, $R^3$ is selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20;

(b) an ω-alkoxypolyalkoxy- group of the formula

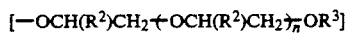
$[-OCH(R^2)CH_2+OCH(R^2)CH_2\overline{)_n}OR^3]$ wherein $R^2$, $R^3$ and n have the hereintobefore ascribed meanings; and, (c) an alkoxy group —$OR^4$ wherein $R^4$ has the hereintobefore ascribed meanings.

(C) and mixtures of (A) and (B).

Examples of compounds of the formula $X_yM^a(OR)_{a-y}(R^1OH)_x$ include but are not limited to $CH_3OMgOCH_2CH_2OCH_2CH_2OC_2H_5$     (a)
$C_6H_{13}OMgOCH(CH_3)CH_2-OCH(CH_3)CH_2OCH_3$
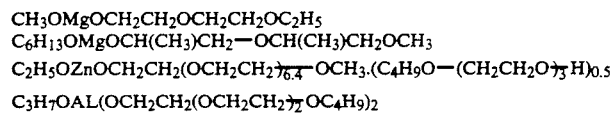
$C_3H_7OAL(OCH_2CH_2(OCH_2CH_2\overline{)_7}OC_4H_9)_2$ $CH_3O(CH_2CH(CH_3)O\overline{)_2}CH_2CH(CH_3)OMgOCH_2CH_2-(OCH_2CH_2)_3OCH_3$     (b)
$C_4H_9O(CH_2CH_2O)_2-CH_2CH_2OZnO-CH(CH_3)CH_2OCH-(CH_3)CH_2OCH_3.(C_2H_5OH)$
$C_2H_5OCH_2CH_2OAl(OCH_2CH_2OCH_2CH_2OC_4H_9)_2$ $(CH_3)_2N-CH_2CH_2OMgOCH_2CH_2OCH_2CH_2OC_2H_5.C_2H_5OH$     (c)
$(C_2H_5)_2NCH_2CH(CH_3)OZnOCH_2CH_2(OCH_2CH_2\overline{)_{6.4}}OCH_3.(C_2H_5)NCH_2CH(CH_3)OH$
$(CH_3)_2NCH_2CH_2OCH_2CH_2OAl(OCH(CH_3)CH_2(OCH-(CH_3)CH_2\overline{)_{72}}OCH_3$ $ClMgOCH_2CH_2(OCH_2CH_2)_3OC_4H_9.C_4H_9O(CH_2CH_2O\overline{)_3}H$     (d)
$BrZnOCH(CH_3)CH_2OCH(CH_3)CH_2OCH_3$
$ClAlOCH_2CH_2(OCH_2CH_2\overline{)_{72}}OC_4H_9$ $C_2H_5OC(O)OMgOCH_2CH_2OCH_2CH_2OC_4H_9$     (e)
$CH_3OC(O)OZnOCH(CH_3)CH_2-O-CH(CH_3)CH_2OCH_{3\cdot 0.5}-(C_4H_9O(CH_2CH_2O)_3H)$
$CH_3OC(O)OMgOCH_2CH_2(OCH_2CH_2)OC_2H_{5\cdot 0.5}-C_4H_9O(CH_2CH_2O\overline{)_3}H$ $C_4H_9MgOCH_2CH_2(OCH_2CH_2\overline{)_{6.4}}OCH_3$     (f)
$C_2H_5ZnOCH_2CH_2(OCH_2CH_2\overline{)_{6.4}}OCH_3$
$C_6H_5Al(OCH_2CH_2(OCH_2CH_2)_2OC_4H_9)_2$ $CH_3CH_2C(O)OMgOCH(CH_3)CH_2OCH(CH_3)CH_2OCH_3.C_2H_5OH$     (g)
$C_4H_9C(O)OZnOCH_2CH_2(OCH_2CH_2\overline{)_{6.4}}OCH_3$
$C_4H_9C(O)OAlOCH(CH_3)CH_2OCH(CH_3)CH_2OCH_3$ Substituted alkoxides, such as zinc or magnesium alkoxides of the above formula (1), wherein II is (a) or (b), dissolved in hydrocarbon or halocarbon solvents are treated, according to this invention, with gaseous carbon dioxide at atmospheric pressure and above, to convert them to carbonated magnesium or zinc alkoxides, (II (e) above) as described in U.S. Pat. No. 3,939,091, col. 3, which discloses passing carbon dioxide into a solution of magnesium methoxide (8 to 9 weight percent) in methanol until the solution or suspension is saturated with carbon dioxide.

Carbonation of the magnesium or zinc alkoxide solutions can be done at temperatures between about 0° and about 100° C. and at pressure between about atmospheric and 1000 psi. Then solvents are stripped from the solution under reduced pressure to yield the neat liquid carbonated magnesium or zinc alkoxides (or alkoxymetalalkoxyalkyl carbonates) shown below. Small amounts (up to 2 moles per mole of carbonated metal alkoxide) of alcohols may be present which are complexed (tightly held) with the carbonated metal alkoxide and are beneficial in promoting solubilization of the carbonated metal alkoxide in the solvents used for treatment of the cellulosic materials.

Examples of the metal alkoxides which can be carbonated with carbon dioxide according to this invention are magnesium and zinc bis-2-alkoxyalkoxides and magnesium and zinc bis-omega (ω) -alkoxypolyalkoxides having the general formula $$R^4O(CH_2CH(R^2)O)_nCH_2CH(R^2)O)_yM\text{-}(OCH(R^2)CH_2(OCH(R^2)CH_2)_mOR^3)_{2-y}\cdot(R^1OH)_x \quad (5)$$

wherein M is selected from magnesium, zinc and mixtures thereof, $R^3$ and $R^4$ are independently selected from $C_1$ to $C_{18}$ hydrocarbyl groups, $R^1$ is selected from $C_1$ to $C_{18}$ hydrocarbyl groups and a $R^3O(CH_2CH_2CH(R^2)O)_nCH_2CH(R^2)$ group, n and m are values from 1 to 20, $R^2$ is selected from hydrogen and methyl, y is a value from 0.01 to 1.0 and x is a value from zero to two.

The resulting carbonated products have carbon dioxide ($CO_2$) incorporated into only one side of the metal alkoxide resulting in a $CO_2/Mg$ ratio of about one, and possessing one of the following two structures;

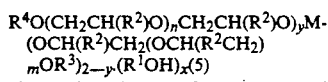

and

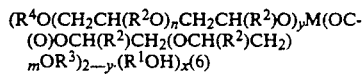

wherein M is selected from magnesium, zinc and mixtures thereof, n and m are values from 1 to 18, $R^2$ is hydrogen or methyl, $R^3$ and $R^4$ are independently selected from $C_1$ to $C_{18}$ hydrocarbyl groups, $R^1$ is selected from $C_1$ to $C_{18}$ to C18 hydrocarbyl groups and a $R^3O(CH_2CH(R^2)O)_nCH_2CH(R^2)$ group wherein $R^3$ is selected from $C_1$ to $C_{18}$ hydrocarbyl groups, y is a value from 0.01 to 1.0 and x is a value from between zero and two and a solvating amount of a solvent selected from aromatic hydrocarbons, halocarbons and mixtures thereof with the proviso that when n and m are equal to one $R^3$ and $R^4$ are hydrocarbon radicals containing more than four carbon atoms. Examples of these carbonated alkoxides are shown in Table 1.

Other magnesium and zinc alkoxides, which are a mixture of the types shown above with aliphatic or cycloaliphatic $C_1$ to $C_{18}$ metal alkoxides may also be half-carbonated to yield novel products of this invention. These metal alkoxides have the general formula:

wherein M is selected from magnesium, zinc and mixtures thereof, $R^3$ and $R^4$ are independently selected from $C_1$ to $C_{18}$ hydrocarbyl groups, $R^1$ is selected from $C_1$ to $C_{18}$ hydrocarbyl groups and $R^3O(CH_2CH(R^2)O)_nCH_2CH(R^2)$, n is value from 1 to 20, $R^2$ is selected from hydrogen and methyl, y is a value from 0.01 to 1.0 and x is a value from zero to two.

The resulting carbonated products possess one of the two following structures:

and

wherein M is selected from magnesium, zinc, and mixtures thereof, n is a value from 1 to 20, y is a value from 0.01 to 1, $R^3$ and $R^4$ are independently selected from $C_1$ to $C_{18}$ hydrocarbyl groups, $R_2$ is selected from hydrogen and methyl, $R^1$ is selected from hydrocarbyl groups having one to eighteen carbon atoms and a $R^3O(CH_2CH\text{-}R^2)O)_nCH_2CH(R^2)$ group wherein $R^3$ is a $C_1$ to $C_{18}$ hydrocarbyl group, $R^2$ is selected from hydrogen and methyl, x is a value from zero to two and a solvating amount of a solvent selected from aromatic hydrocarbons, halocarbons and mixtures thereof. Examples of these carbonated metal alkoxides are shown in Table 2.

Aluminum and zinc alkoxides can be added to these carbonated compositions and to the other carbonated compositions of this invention to help solubilize the components of the compositions.

The products of the invention may be prepared via a number of techniques, known to the art, such as by reacting a suspension of magnesium metal, or magnesium amide or $C_1$–$C_3$ magnesium dialkoxides in a hydrocarbon or halocarbon solvent, or by reacting a solution of a dialkylmagnesium or a dialkylzinc compound in a hydrocarbon solvent, with a 2-alkoxy-substituted alkanol (ROCH$_2$CHR'OH) wherein R is a $C_1$–$C_{12}$ hydrocarbyl and R' is hydrogen or methyl; or a member of the group of ω-alkoxy-poly(alkoxy)alkanols, of the formula RO(CH$_2$CH(R')O)$_n$CH$_2$CH(R',)OH wherein R is a $C_1$–$C_{18}$ hydrocarbyl group, R' is a methyl group or hydrogen, and n is from 1 to about 100, and carbonating the products thereof.

The 2-alkoxyalkanols (ROCH$_2$CHR'OH) where R is hydrogen, also have the trade name Cellosolves (Union Carbide) and are exemplified by the substances Methyl Cellosolve TM (CH$_3$OCH$_2$CH$_2$OH), Butyl Cellosolve TM (C$_4$H$_9$OCH$_2$CH$_2$OH) and Hexyl Cellosolve (C$_6$H$_{13}$OCH$_2$CH$_2$OH).

The ω-alkoxypoly(alkoxy)alkanols, of the formula (RO(CH$_2$CH(R)O)$_n$CH$_2$CH(R')OH), where n is one and R' is hydrogen, also have the trade name Carbitol and are exemplified by the substances Methyl Carbitol, Butyl Carbitol and Hexyl Carbitol. Higher n numbers, e.g. where n is 2, give Methoxy, Ethoxy, and Butoxytriglycol, and where n is 6 or more, Methoxy Polyethylene Glycols (trademark Carbowax MPEG, Union Carbide).

These can be used in mixtures thereof with each other or with $C_1$ to $C_{12}$ alcohols selected from the group of (a) aliphatic 2-alkyl-substituted $C_4$–$C_{12}$ primary monohydric alcohols; or (b) aliphatic $C_3$–$C_{12}$ secondary or tertiary alcohols; or (c) aliphatic $C_1$–$C_{12}$ primary linear unsubstituted alcohols; and removing hydrogen or ammonia which forms during the reaction.

The starting magnesium or zinc alkoxide may also be prepared by reacting a solid magnesium or zinc dialkoxide of the formula $Mg(OR)_2$ or $Zn(OR)_2$ in which R is a $C_1$–$C_{12}$ hydrocarbyl group, with at least two molar equivalents of a 2-alkoxy-substituted alkanol, $ROCH_2CHR'OH$, or an $\omega$-alkoxypoly(alkoxy)alkanol, $RO(CH_2CH(R')O)_nCH_2CH(R')OH$ wherein R is a $C_1$–$C_{12}$ hydrocarbyl group and R' is hydrogen or a methyl group, and n is from 0 to about 100, isolating the resultant mobile liquid product, and dissolving same in a hydrocarbon or chlorinated hydrocarbon or halocarbon solvent of choice, or by reacting a solid magnesium dialkoxide with just one molar equivalent of a 2-alkoxyalkanol or $\omega$-alkoxypoly(alkoxy)alkanol in a hydrocarbon or halocarbon solvent, or by reacting dialkylmagnesium or dialkylzinc compounds of the formula $MgR_2$ or $ZnR_2$ in which R is a $C_1$–$C_{12}$ hydrocarbyl group, with at least two molar equivalents of a 2-alkoxy-substituted alkanol, $ROCH_2CHR'OH$, or $\omega$-alkoxypoly(alkoxy)alkanol or mixtures of such alkanols, in which R is a $C_1$–$C_{12}$ hydrocarbyl group and R' is hydrogen or a methyl group, some typical examples of which are as described in U.S. Pat. No. 4,634,786, incorporated herein by reference, and then carbonating the product thereof.

After carbonation is complete, as evidenced by no further evolution of heat, the resulting liquid products and solutions thereof of the magnesium or zinc alkoxide carbonates are unexpectedly more fluid (less viscous) than the original magnesium or zinc alkoxide products and solutions before carbonation, especially in the case of the higher homologs where n is greater than one; this is evident even after complete removal of solvents. For example, a sample of magnesium butoxytriglycolate (n=2) in heptane (before carbonation) was stripped of solvent and found to be so extremely viscous that the product would not flow. Even after addition of 20 weight percent of hexane, the product was still not fluid enough to pour. On the other hand, another sample of the same magnesium butoxytriglycolate, after carbonation and stripping, yielded a completely fluid, low viscosity liquid residue, which was readily pourable and which formed fluid pourable solutions in hexane at all concentrations. (Similar results are evident when zinc is used in place of magnesium.)

Comparison of this thinning effect on carbonation of the magnesium alkoxides of this invention with the result obtained on carbonation of other hydrocarbon-soluble magnesium alkoxide types described in U.S. Pat. No. 4,634,786 (magnesium 2-alkyl-substituted alkoxides) and hydrocarbon soluble magnesium/aluminum alkoxide complexes described in U.S. Pat. Nos. 4,246,383, 4,426,316, and 4,244,838 is striking. Treatment of a 0.6M solution of magnesium 2-methylpentyloxide solution in heptane with carbon dioxide, resulted in a solid gel while a much lower concentration of the same compound gave a precipitate rather than a solution on carbonation. In another case, a sample of a 1:1 complex of magnesium and aluminum n-butoxides dissolved in heptane/hexane was carbonated resulting in gelation of the solution. Neither gelation nor precipitation leads to a useful product for the purpose of evenly treating cellulosic materials. Alcoholic co-solvents which might aid in dissolving these products are not desirable for the purpose of deacidifying paper and books, as was mentioned earlier.

The carbonpated magnesium or zinc alkoxides of this invention possess the property of essentially complete miscibility in a variety of normally liquid hydrocarbon solvents such as, for example, pentane, hexane, heptane, benzene, toluene, and cyclohexane as well as gaseous hydrocarbons such as ethane, propane, propylene and butanes. In addition, said carbonated magnesium or zinc alkoxides are soluble in normally liquid halocarbons, such as 1,1,2-trichlorotrifluoroethane, symmetrical tetrachlorodifluoroethane, perchlorethylene, chloroform and methylchloroform and mixtures thereof. Other gaseous halocarbons contemplated as solvents are chlorotrifluoromethane, chlorodifluoroethane and 1,2-dichlorotetrafluoroethane.

Another property inherent in the carbonated magnesium or zinc alkoxides of this invention is the great expandability of their volumes either alone or in solution on treatment with certain gases such as, for example, the hydrocarbon gases ethane, propane, and butane, or the chlorofluorocarbon or fluorocarbon gases such as fluoroform, hexafluoroethane, tetrafluoroethane, perfluoropropane, chlorotrifluoroethane, chlorodifluoroethane and 1,2-dichlorotetrafluoroethane and even gases such as carbon dioxide. This property of solution expandability was found to be useful in the treatment of cellulosic materials such as paper and books. Although solution expandability on gasification is not a new concept, it has been noted that such solution expansion must be controlled by judicious pressure regulation so as not to exceed the solubility of the magnesium or zinc compound in the combination of gaseous and liquid solvents. Beyond a certain pressure precipitation of the dissolved magnesium or zinc compounds occurs, leading to a non-homogeneous deposition of a deacidifying agent on the books. For example, ethane gas reproducibly gave expanded solutions of the magnesium or zinc compounds of this invention to at least twice their original volume under pressures of 500 psi or less without thickening or precipitation of the solutions. In addition, the original volume of ungasified solution could be reversibly generated by venting of the dissolved ethane gas. It is important to note that precipitation of the magnesium compounds of this invention can be made to occur using ethane by raising the pressure above about 500 psi (pressure depends upon the concentration of magnesium in the original solution and its solvent composition), but is undesirable for the purpose of treatment of cellulosic materials, leading to streaky, sticky finishes.

Similarly, carbon dioxide gas expands perchloroethylene solutions of the carbonated magnesium or zinc alkoxides to over twice their original volume at pressures not much above 650 psi.

Thus, this property of expandability of hydrocarbon and halocarbon solutions of the magnesium or zinc compounds of this invention was found to be applicable to the treatment of cellulosic materials such as paper and books, by the simple expedient of suspending the cellulosic materials just above the level of the liquid hydrocarbon solutions of the magnesium or zinc compounds, pressurizing the hydrocarbon or halocarbon solutions with ethane or carbon dioxide gas to an internal pressure of about 500 psi (650 psi for $CO_2$), so as to cause the original solution volume to expand sufficiently (at least double) to cover the said cellulosic material, and, after a sufficiently long treatment time, to vent the dissolved ethane or carbon dioxide gas, thus reducing the volume of the hydrocarbon (or halocarbon) solution to its original volume and below the level of the treated cellulosic material. On removal from the pressure chamber, the treated cellulosic material was found to be dry and possessed a satiny smooth finish. Any number of consecutive treatments of the cellulosic material for varying lengths of time as described above can be carried out so as to impart the desired protective finish to the cellulosic material simply by alternatively expanding and contracting the hydrocarbon or halocarbon solution. Thus, for example, although single pieces of paper receive a deacidifying finish with as little as one such expansion/contraction cycle for as short a contact time as 15 seconds, multiple pieces of paper such as book pages may require several such cycles with longer contact time periods.

Generally, a pressure range for the carbonated magnesium alkoxide solution "expanding" gas should be from about 100 psi to about 1000 psi. Supercritical gas pressure or temperatures are not required. In addition, elevated temperatures above ambient are not required during the expansion/contraction phases of the treatment of cellulosic materials.

It is also possible to use the hydrocarbon or halocarbon solutions of the carbonated zinc and magnesium alkoxides directly as deacidifying media, that is, without gaseous expansion. Thus, an approximately 8 volume/volume % (v/v%) solution of magnesium butoxytriglycolate (MBTG) in Freon TF (1,1,2-trichlorotrifluoroethane) was used to treat pages taken from a book, under various conditions, and found to evenly penetrate the pages, leaving about a 2% residual buffer of magnesium, calculated as $MgCO_3$. Strengthening of the pages was shown by an increase in the number of folds required to break a page in half (parallel to the binding) in the treated vs. the untreated samples, of about 400%. Other solvents may also be used, as mentioned above.

The concentration of the metal ion in the deacidifying treatment medium may be varied widely, but generally will lie in the range of 0.01 to 1.0 molar. More preferably, the range of metal ion concentration will lie in the range of 0.02 to 0.5 molar and, most preferably, 0.05 to 0.25 molar. Sufficient metal ion, calculated as $MgCO_3$, is generally desirable to provide about 2% $MgCO_3$ as both deacidifying agent and residual buffer, although this value may not be as critical where additional strengthening of the cellulosic material is being provided as by the products of this invention.

Naturally, the effects of time of treatment (treatment cycle) and number of treatment cycles is an important consideration and will also affect the metal ion concentration being deposited. Thus, in certain single page treatments, although about 2-5 minutes sufficed to give pages containing 2% of $MgCO_3$ (equivalent), a 10 minute treatment time gave pages with the most even distribution of $MgCO_3$.

Another factor controlling metal ion deposition which needs to be empirically determined in each case is the type of cellulosic material being treated, which material can vary widely in composition.

As mentioned earlier for the gaseous expansion process, temperature and pressure will also play a role in metal ion deposition, and it is expected that higher values of both will promote (increase) metal ion concentrations in the treated products.

For such treatments, generally short cycles are preferable, of the the order of an hour or so or less, depending on the number and thickness of the items being treated, and on the porosity of the cellulosic material the items are made from. Thus, a 3 inch by 3 inch by 1 inch thick book containing porous paper was uniformly treated in 10 minutes, with a page taken from the center of the book showing the presence of about 1.5% $MgCO_3$.

It is believed that the magnesium and zinc compounds of this invention possess a unique chemical structure which can readily complex (associate) with the many hydroxyl groupings in cellulosic materials, thus binding the magnesium or zinc compounds tightly to the cellulosic materials and providing the latter with an additional (to deacidification) protective film or coating. As the number of ethoxy or propoxy units in the magnesium or zinc compounds increases, it has been found that the film or coating provided will also impart a strengthening property to the cellulosic material.

Thus, for example, the number of folds before breakage of pages taken from an old book which had been previously treated with the following magnesium alkoxide carbonates in a Freon TF Solution increased as shown:

| Magnesium Alkoxide (Carbonate) | as the No. of folds to break |
|---|---|
| Magnesium Butoxytriglycolate | 29 |
| Magnesium Butoxytriglycolate/ Methoxypolyethoxide[a] | 35 |
| Magnesium Bis-Methoxypolyethoxide | 59 |
| None | 5 |
| Magnesium Methoxide | 4 |

(a) number of ethoxy units is an average of 7.4.

In contrast to previously utilized carbonated magnesium alkoxides (such as methoxymagnesium methyl carbonate) treatments where no strengthening effect is noted, not only do the magnesium salts of this invention adhere to the cellulosic structure of the paper, but the by-products of the deacidification process, the ω-alkoxy(poly)ethoxy and ω-alkoxy(poly)propoxy alcohols themselves, also do so. Thus, there is no massive venting of volatile alcohols, such as methanol, from the pages of a book during the continuing deacidification processes that may occur on library bookshelves in a book with the passage of time.

Metallic alkoxides of the type shown above for magnesium and zinc, but without carbonation, can also be used in such treatments, either alone, or in admixture with the carbonated magnesium and zinc alkoxides. Thus, for example, aluminum alkoxyalkoxides and ω-alkoxypolyalkoxides can be prepared in pure liquid form and used alone or in admixture with the carbonated magnesium and zinc alkoxyalkoxides and alkoxypolyalkoxides described above. Typical aluminum alkoxides of this type are aluminum trishexylcarbitolate, aluminum tris-ω-methoxypolyethoxide, ethoxyaluminum bis-ω-methoxypolyethoxide, and the like.

Other partially alkoxylated alkylmetallic compounds may also be used in solution form to treat cellulosic materials. These alkylmetallic alkoxides have the generic formula:

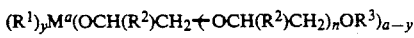

wherein M is Mg, Zn, and Al and mixtures thereof, $R^1$ and $R^3$ are $C_1$ to $C_{18}$ hydrocarbyl, $R^2$ is hydrogen or methyl, n is a value from 1 to 20, y is a value between 0.01 and 1.0, and a is the valence of the metal. Examples of these compounds are shown in Table III, below:

TABLE III

| $M^a$ | $R^1$ | $R^2$ | $R^3$ | n | y |
|---|---|---|---|---|---|
| Zn | $C_2H_5$ | H | $CH_3$ | 6.4 | 1.0 |
| Al | $i-C_4H_9$ | H | $CH_3$ | 6.4 | 1.0 |
| Mg | $n,s-C_4H_9$ | H | $CH_3$ | 6.4 | 1.0 |
| Mg/Al = 2 | $C_4H_9$ | H | $CH_3$ | 6.4 | 1.0 |
| Zn/Al = 1.5 | $C_2H_5/iC_4H_9$ | H | $CH_3$ | 6.4 | 1.0 |

Thus, for example, a solution of ethylzinc-ω-methoxypolyethoxide in a halocarbon solution was used to treat books and found to give a uniform distribution of zinc in a page taken from the center of a book at a level of 1.5–1.7% zinc oxide.

Other such typical alkylmetal alkoxides which may be used alone or in combination with each other in solution form to deacidify and strengthen cellulosic materials are butylmagnesium ω-methoxypolyethoxide, isobutylaluminum bis-ω-methoxypolyethoxide and ethylzinc butoxytriglycolate. It should be noted that the aluminum compounds, generally should not be used alone since they have a strong propensity toward hydrolysis.

In some cases it has been found that combinations of two or more of such alkylmetal alkoxides possess improved properties. Thus, for example, addition of an equivalent amount of isobutylaluminum-bis-ω-methoxypolyethoxide to butylmagnesium-ω-methoxypolyethoxide pacifies the latter's normal reactivity with halocarbon compounds to such an extent that a solution of these two metal alkoxides can be prepared containing a high concentration of Freon TF.

In some cases, these alkylmetal alkoxides may act to improve the solubility of the carbonated magnesium and zinc alkoxides in certain solvents such as Freon TF. Thus, for example, addition of an equal amount of isobutylaluminum bis-ω-methoxypolyethoxide to zinc bismethoxypolyethoxide (carbonated) improves the latter's solubility in Freon TF. By contrast, a Freon TF solution of aluminum isopropoxide did not promote the solubility of magnesium ethoxide in the same solvent. Such blends of metal alkoxides give deacidifying media which are milder buffers than magnesium alkoxides alone.

Also contemplated are the halometalalkoxides, $X_yM^aOR_{a-y}.(R'OH)$, wherein X is a halogen, preferably chlorine or bromine, M is a metal of Periodic Groups IIA, IIB, or IIIA, OR is an alkoxy group wherein R is an alkyl, cycloalkyl, aryl, arylalkyl or alkylaryl, or an alkoxyalkoxy group, particularly a 2-alkoxyalkoxy- or ω-alkoxypoly(alkoxy) group, a is the valence of the metal, y is a value from 0.01 to about 1 and X is 0 to 2.

Examples of such halometalalkoxides are chloromagnesium butoxyethoxide, chloromagnesium ω-methoxypolyethoxide, chlorozinc ω-methoxypolyethoxide, chloroaluminum bis-ω-butoxytriglycolate, and mixtures thereof.

A novel procedure for preparing such halometal alkoxides has been developed which involves reaction of the desired alcohol and metal in the presence of a minor quantity of methanol, and an equivalent quantity of fluorochlorocarbon such as 1,1,2-trifluorotrichloroethane (Freon TF) in a hydrocarbon solvent. The halocarbon functions as a halogenating agent in the process:

The hydrocarbon solution is filtered and stripped, if desired, to give residual liquid products, which can be redissolved in various solvents, described above.

Also contemplated are acyloxymetal alkoxyalkoxides, $(R^4C(O)O)_yM(-OCH(R^2)CH_2(OCH(R^2)CH_2-)_nOR^3)_{2-y}.(R'OH)_x$ and alkoxypolyalkoxides in which $R^4$ is a $C_1$ to $C_{18}$ alkyl, aryl, cycloalkyl, arylalkyl, or alkylaryl group, M is a divalent metal from Groups IIA and IIB of the Periodic Table, R' is a $C_1$ to $C_{18}$ alkyl, aryl, cycloalkyl, arylalkyl, or alkylaryl group, or is alkoxyalkoxy or alkoxypolyalkoxy derived from the alkoxide, where $R^2$ is a methyl group or hydrogen and R' and R" are the same or different alkyl, aryl, cycloalkyl, arylalkyl and alkylaryl, y is a value from 0 to about 1 and x is a value from 0 to 2.

Also contemplated are magnesium and zinc mono- and dialkylaminoethoxides and dialkylaminopolyalkoxides such as, e.g., magnesium or zinc bis-N-methylaminoethoxide and magnesium or zinc bis-N,N-dimethylaminoethoxide, and their higher homologs,

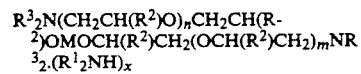

where n and m are greater than 1 and $R^2$ may be H or $CH_3$ and $R^1$, and $R^3$ may be the same or different $C_1$-$C_{18}$ hydrocarbyl groups.

The following examples further illustrate the invention.

EXAMPLES

Example I—Preparation of Carbonated Magnesium n-Hexyl-oxyethoxide
$C_6H_{13}OCH_2CH_2O-Mg-OC(O)OCH_2CH_2O-C_6H_{13}$
("A")

To a solution of 292.5 g (2.0 mole) of ethyleneglycol, monohexyl ether (n-hexylcellosolve) dissolved in 850 ml heptane was slowly added 1.02 liters of a solution of dibutylmagnesium in heptane (19.2 weight percent). After reaction was complete, the solution was filtered and carbon dioxide passed into it through a gas inlet tube from a one liter flask containing pieces of dry ice. The gas was passed through two drying columns containing calcium chloride before entering the gas inlet tube. The temperature of the solution in the flask rose from 31° to 42° C. during the carbonation. After reaction was complete, as noted by a significant drop in the reaction temperature, the solution was stripped of solvent on a ROTO-VAC apparatus and the residual fluid, somewhat viscous mass, transferred to a pint bottle under inert gas (argon). The weight of recovered product was 307 g (87% recovery).

Another 0.11 mole preparation of magnesium n-hexyloxyethoxide using magnesium ethoxide in place of dibutylmagnesium was carried out and the solvents (ethanol and heptane) removed by vacuum stripping. The viscous residue was redissolved in hexane (to about 0.9M) and carbonated as described above. The temperature during carbonation rose from 24.3° to 39.8° C. After 1.25 hours of slow CO₂ feed, the temperature had returned to 23° C. The solution was vacuum stripped to give a viscous mobile liquid that readily dissolved in hexane. Only a trace (<0.01%) of ethanol remained. An infrared scan of the residue dissolved in hexane showed a strong absorbence at 6 microns indicative of a carbonyl group. Analysis of the solvent-stripped residue for contained CO₃ gave a value of 16.5%, Corresponding to a CO₃/Mg ratio of 1.01.

Example II—Preparation of Carbonated Magnesium Hexyloxyethoxyethoxide
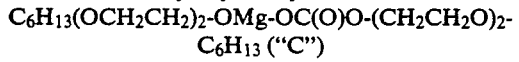

To 71.5 ml of a 27.4 weight percent solution of dibutylmagnesium in heptane (0.1 mole) in 100 ml of hexane was slowly added 41 ml (0.2 mole) of n-hexylcarbitol (neat). A clear, viscous solution was obtained upon cooling to room temperature. Carbonation of the solution with carbon dioxide gas thinned out the solution considerably. The resulting product was stripped of solvent to give 35 grams of a fairly fluid, somewhat viscous clear yellow mobile (pourable) liquid (87% recovery).

Example III—Preparation of Carbonated Ethoxymagnesium ω-Methoxypolyethoxide
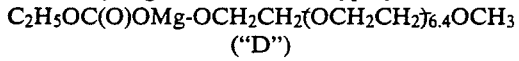

To 71.5 ml of a 27.4 weight percent solution of dibutylmagnesium in heptane (0.1 mole) contained in 100 ml of toluene was slowly added 30 ml (0.093 mole) of methoxypolyethyleneglycol (CH₃O(CH₂CH₂O)₇.₄H, Union Carbide Corp. MPEG 350). A clear, slightly hazy solution of the alkyl magnesium alkoxide resulted.

Two 10 ml aliquots of the solution (approx. 0.004 mole each) were taken and treated as follows:

(a) Carbonated with CO₂—a clear very fluid solution was obtained on carbonation.

(b) Alkoxylated with ethanol. Sufficient ethanol (about 0.2 ml) was added to the aliquot to dissipate the red color generated by a small amount of 2,2'-biquinoline indicator. A thick, extremely viscous clear solution resulted, which on subsequent carbonation thinned out almost immediately to give a pale yellow clear, non-viscous solution.

Treatment of the remainder of the main alkylmagnesium alkoxide solution as in (b) above, followed by solvent stripping of the carbonated magnesium alkoxide solution yielded 34 grams of a pale yellow, slightly hazy, mobile, somewhat viscous but pourable, liquid residue, which dissolved readily in toluene, but not in hexane. To 8.3 grams of carbonated ethoxy magnesium-1-methoxypolyethoxide was added 45 ml of Freon TF to give a 2 phase mixture. Addition of 0.8 grams of butoxytriglycol gave an almost clear solution, while a further addition of 0.8 g of butoxytriglycol gave a clear solution. Thus, as little as 20–50 mole % (10–25 wt. %) of butoxytriglycol will promote solubility of ethoxy magnesium-ω-methoxypolyethoxide in Freon TF.

In the formula for "D" above, carbonation could as well have been shown to take place on the methoxy-ω-polyethoxide side of the molecule.

Example IV—Preparation of Carbonated Magnesium Butoxytriolycolate
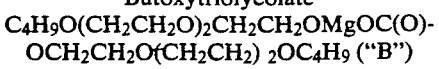

(a) To 25 mls (0.031 mole) of 1M dibutylmagnesium in hexane solution plus an additional 50 ml of hexane was slowly added 12.8 g pure butoxytriglycol (Union Carbide Corp.). The solution remained clear and fluid throughout. After approximately 0.5 hours, carbon dioxide was passed through the solution to form the alkoxide carbonate. The final solution was clear and fluid at about 0.35M Mg and was solvent stripped on the ROTO-VAC apparatus for 1 hour at 70° C. The concentrated solution was viscous, but fluid (mobile). An infrared scan of a hexane solution of the product showed a new band at 6.0 microns.

(b) To 27.7 grams (1.14 g.at.) of magnesium powder in 850 ml of n-heptane activated with 0.2 g of iodine and heated to 90° was added 10 ml of a mixture of 362 g (1.75 moles) of butoxytriglycol and 24 g (0.52 mole) of ethanol. Reaction was slow, so an additional 15 g of magnesium metal in the form of chips was added and heating resumed. After a time, reaction began slowly and mixed alcohol feed was continued. After the reaction was completed, about half the mixture was filtered (slow filtration) to give a rather viscous, clear, yellow solution. The remainder of the unfiltered mixture was carbonated and the resulting mix became quite fluid and was easily filtered. After carbonation of the first half of the solution (thinning of solution), the solutions were combined and solvent-stripped to yield 368 grams of a viscous, but mobile, pourable product.

The carbonated solution of magnesium butoxytriglycolate in heptane prior to stripping was approximately 0.9 molar in magnesium concentration, but about 50 weight percent in carbonated product, showing the high concentrations of these magnesium compounds attainable. Some of the magnesium butoxytriglycolate from a previous run, which had not been carbonated, was also solvent stripped. The resulting product was extremely viscous (not mobile) even with the addition of 20% by weight of hexane, thus demonstrating the unexpected decrease in viscosity of these magnesium alkoxide solutions on carbonation.

The carbonated product was analyzed for carbonate (CO₃) content and found to contain 16.21 weight percent which corresponded to a CO₃/Mg ratio of 1.02. Infrared analysis showed a strong absorption in the 6.0–6.1 micron frequency region.

Example V—Preparation of Carbonated Magnesium Butoxy 2-Propoxide

0.025 Mole (18 ml) of 27.4 weight percent DBM in heptane and 25 ml of hexane were placed in a flask and 7.5 ml (0.05 moles) of butoxy-2-propanol Propasol B (Union Carbide Propasol B, MW=32.2,d=0.8843) added dropwise with stirring. The solution remained hazy almost throughout the addition, then cleared up near the end of the addition to give a clear colorless, somewhat viscous solution. The product was carbonated and the viscosity of the solution appeared to decrease as evidenced by the greater stirring speed of the magnetic stirring bar.

Example VI—Preparation of Carbonated Hexyloxyethoxymagnesium ω- Methoxypolyethoxide (MPEG 350)
C₆H₁₃OCH₂CH₂OC(O)OMgOCH₂CH₂(OCH₂CH₂)₆.₄OCH₃

To 0.25 mole (18 ml) of 27.4 weight percent dibutylmagnesium solution in heptane (DBM) and 25 ml of hexane, was slowly added 8 ml (0.025 mole) of MPEG 350. (Union Carbide Methoxypolyethylene glycol, MW=335-365). Next 4.1 ml (0.025 mole) of hexylcellosolve was added to yield a milky solution which slowly separated into two clear, colorless, mobile liquid layers. Next, the following amounts of DBM and hexylcellosolve (HC) were added in consecutive fashion: 9 ml (0.0125 mole) DBM, 4.1 ml (0.025 mole) HC, 9 ml DBM, 4.1 ml HC, 4.5 ml DBM, 2.05 ml HC, 4.5 ml DBM, 2.05 ml HC. The total DBM added to this point was 0.0625 mole, total hexylcellosolve was 0.100 mole and MPEG 350, 0.025 mole (ratio HC/MPEG=4.0). A clear, colorless solution was obtained at warmer than room temperatures, but a small amount of a second phase separated on cooling to room temperature. On carbonation, some decrease in viscosity was noted, but solvent evaporation occurred during carbonation to give a slightly viscous, approximately 1 molar solution which was crystal clear and colorless even at room temperature. In the formula above, carbonation could as well have been shown to take place on the methoxy ω-polyethoxide side of the molecule.

Example VII—Preparation of Carbonated Hexyloxyethoxyethoxymagnesium ω-Methoxypolyethoxide
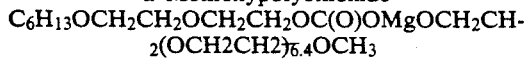
C₆H₁₃OCH₂CH₂OCH₂CH₂OC(O)OMgOCH₂CH₂(OCH₂CH₂)₆.₄OCH₃

To 0.025 mole (18 ml) of DBM (27.4 Weight percent in heptane) and 25 ml hexane was slowly added 8.1 ml (0.040 mole) of diethylene gylcol monohexyl ether (Hexyl Carbitol™ UCC) followed by 3.2 ml (0.01 mole) of MPEG 350. A clear, pale yellow fluid solution was obtained which, on carbonation, became even more fluid (less viscous). In the formula above, carbonation could as well have been shown to take place on the methoxy ω-polyethoxide side of the molecule.

Example VIII—Preparation of Carbonated Magnesium Propoxy 2-Propoxide
C₃H₇OCH₂CH(CH₃)OMgOC(O)OCH(CH₃)CH₂OC₃H₇

To 0.025 mole (18 ml) of DBM (27.4 weight percent) and 25 ml hexane was slowly added 6.6 ml (0.05 mole) of propoxy 2-propanol (UCC Propasol P). The solution remained hazy almost throughout the addition, then cleared up to give a colorless, slightly viscous, mobile solution. Carbonation decreased the viscosity of the solution.

Example IX—Preparation of Zinc Hexyloxyethoxyethoxide
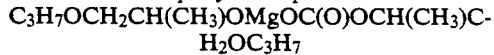
C₆H₁₃OCH₂CH₂OCH₂CH₂OZnOCH₂CH₂OCH₂CH₂OC₆H₁₃

To 50 ml of a 14.4 weight per cent solution of diethylzinc in hexane (density=0.708) was added 16.8 ml (15.7 g, 0.082 m) hexyl carbitol (Union Carbide). Ethane was evolved during the addition and the temperature of the reaction mixture reached 55°-60° C. After addition was complete, the mixture was heated to reflux for 30 minutes and then solvent was stripped on a ROTO-VAC unit to 80° C. under full vacuum (<1 min.). A deep amber, clear, viscous, but quite mobile liquid was obtained. Carbonation of a solution of this product in hexane at room temperature did not form a carbonate as evidenced by CO₂ evolution on treatment with aqueous HCl.

A repeat of the above preparation using milder temperatures (<30° C.) yielded a light yellow colored, less viscous product.

Example X—Preparation of Aluminum Hexyloxyethoxyethoxide
Al(OCH₂CH₂OCH₂CH₂OC₆H₁₃)₃

A volume of 27 ml (25 g, 0.1325 m) of hexyl carbitol (Union Carbide) was added slowly to a solution of 50 ml of 25 weight per cent triisobutylaluminum in hexane (density 0.70). Isobutane was evolved and the solution heated to 55°-60° C. The reaction mixture was then refluxed for 30 minutes and stripped of solvent under vacuum in a ROTO-VAC unit. The residual product was a fluid, slightly viscous, light yellow colored oil (24.5 grams).

Example XI—Preparation of Carbonated Magnesium-bis-ω-methoxypolyethoxide
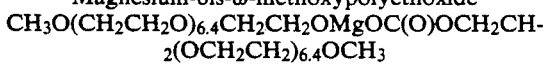
CH₃O(CH₂CH₂O)₆.₄CH₂CH₂OMgOC(O)OCH₂CH₂(OCH₂CH₂)₆.₄OCH₃

To 50 ml of a 1.3 molar solution of dibutylmagnesium in heptane (0.065 m) and 70 ml of toluene containing a small amount of 2,2′-biquinoline indicator, was added, slowly, 42 ml (46 g) of methoxypolyethylene glycol (Union Carbide MPEG 350) with stirring and cooling to a somewhat hazy, light yellow solution. The product was then treated with dry carbon dioxide gas for approximately one hour to give a clear solution. The solution was stripped under vacuum to a yellow-green, somewhat hazy mobile, viscous liquid (41.5 g).

A solution of this product in Freon TF could be prepared by admixture of as little as 14 wt. % (50 mole %) of butoxytriglycol.

Example XII—Preparation of Carbonated Butoxytriglycoxymagnesium-ω-methoxypolyethoxide
C₄H₉O(CH₂CH₂O)₂CH₂CH₂OC(O)OMgOCH₂CH₂(OCH₂CH₂)₆.₄OCH₃

(a) To 54 ml of a 1.3 molar solution of dibutylmagnesium in heptane and 50 ml of toluene was added 22.4 ml (24.5 g, 0.07 m) of methoxypolyethylene glycol (MPEG 350, Union Carbide) and 14.4 ml (14.4 g, 0.07 m) of butoxytriglycol (Union Carbide). The solution stayed clear and fluid throughout the addition. The solution was carbonated to give a clear, fluid light colored solution. After stripping under vacuum to remove solvent, a weight of 43.7 g was obtained, which readily dissolved in Freon TF.

In the above formula, carbonation could have been shown to take place on the ω-methoxypolyethoxide group.

Example XIII—Preparation of Ethyl Zinc ω-methoxypolyethoxide (EZMPG)
C₂H₅ZnOCH₂CH₂(OCH₂—CH₂O)₆.₄OCH₃

To 121 ml of a 14.4 weight percent solution of diethylzinc in hexane (0.10 mole) was added slowly, 31.9 ml (35 g, 0.10 mole) of methoxypolyethylene glycol (MPEG 350, Union Carbide), keeping the temperature below 30° C. with cooling. After stirring for an additional 45 minutes, the milky solution (2 layers) was vacuum stripped to remove hexane (only one liquid layer after strip). A grayish hazy liquid (39 g) was obtained which was dissolved in toluene, the solution was allowed to settle, and the clear supernatant decanted and again stripped to remove toluene. 35 g of an almost clear, water white fluid product was obtained, which slowly gave off a gas (bubbled) on hydrolysis or exposure to air, but did not spontaneously ignite. To 33 grams of EZnMPG was added 100 ml of Freon TF to give a slightly hazy solution.

Example XIV—Preparation of Isobutylaluminum-ω-methoxypolyethoxide $C_4H_9Al(OCH_2CH_2(OCH_2CH_2)_{6.4}OCH_3)_2$ To 113 ml of a 25 weight per cent solution of triisobutylaluminum in hexane (0.10 mole) was slowly added 69.4 ml of methoxypolyethylene glycol (MPEG 350, Union Carbide). The solution became milky and eventually formed two layers. Addition of 75 ml of toluene gave a clear solution. The solution was then vacuum stripped to remove solvents. A fluid, colorless, slightly hazy liquid (68 g) was recovered, which readily dissolved in Freon TF to give a clear solution.

Example XV—Preparation of Butylmagnesium ω-methoxypolyethoxide $C_4H_9MgOCH_2CH_2(OCH_2CH_2)_{6.4}OCH_3$ To 113 ml of a 0.97 m solution of dibutylmagnesium in heptane and 50 ml of toluene was added, with cooling, 35 ml (0.11 m) of MPEG 350 (Union Carbide). The mixture was then stirred for 2 hours and allowed to settle overnight. Two liquid layers were obtained, the lower layer containing 92% of the magnesium content. The upper layer was separated and discarded. 20 ml of toluene was added and the lower layer was vacuum stripped to give a clear orange-colored viscous liquid (42.3 g), which was very reactive to air and moisture, but not pyroforic. It reacted vigorously with Freon TF. However, when mixed with an equivalent amount of Isobutylaluminum ω-methoxypolyethoxide, only a very slight, if any, reaction with Freon TF was noted, indicating passivation of the carbon-magnesium bond and good solubility in Freon TF with potential for book deacidification.

Example XVI—Preparation of Carbonated Zinc bis-ω-methoxypolyethoxide $CH_3O(CH_2-CH_2O)_{6.4}CH_2CH_2OZnOC(O)OCH_2(OCH_2CH_2)_{6.4}OCH_3$ To a volume of 139 ml (0.115 mol) of a 14.4 weight percent solution of diethylzinc (DEZ) in hexane and 75 ml toluene was slowly added 80.5 g (0.23 mol) of methoxypolyethylene glycol (Average Mol. Wt.=350) at 25°–30° C. The mixture (2 layers) was stirred 45 minutes after the DEZ addition was complete. The product mixture was vacuum stripped to remove solvent, but became extremely viscous and would not flow. The product mass was redissolved in hot toluene (40°–50° C.) and carbonated. Heat was generated as carbonation proceeded. The product solution was again vacuum-stripped to give a much less viscous, pourable product. An infrared spectrum of the neat product showed bands at 5.15 (ms), 5.40 (ms), 5.55 (ms), 5.75(w), and 6.25 (s) microns, all indicative of carbonyl groupings. There were no absoprtions in the 2.75–3.25 microns region indicative of hydroxyl groups. The product was not soluble in Freon TF; however, addition of 5 volume per cent chloroform gave a clear solution containing 5 volume per cent product. Admixture of the neat product with an equal volume of isobutylaluminum bis-ω-methoxypolyethoxide followed by Freon TF addition gave a fluid upper layer containing 67 vol % of metal MPEG compounds in Freon TF, indicating a solubilizing assistance of the aluminum compound.

Example XVII—Preparation of Carbonated Methoxymagnesium ω-ethoxytriolycolate in Freon TF 0.131 moles (11.30 g) of $Mg(OCH_3)_2$, 85 ml of Freon TF and 0.131 moles (23.2 g, 23 ml) of of ethoxytriglycol (Union Carbide Corp.) were mixed together and stirred for 30 minutes. Carbon dioxide was sprayed into the thick mass, causing the mix to thin and to become almost clear. An additional 40 ml of Freon TF was added along with 13.5 ml (0.066 moles) of butoxytriglycol and the solution diluted to 650 ml with Freon TF to give a 0.2 molar solution of the title compound.

Comparison Freon TF Solubility Test—Magnesium Ethoxide/Aluminum Isopropoxide One gram (5 mmoles) of aluminum isopropoxide was dissolved in 10 ml of Freon TF solvent and 0.7 grams (6 mmoles) of magnesium ethoxide added. After mixing in an ultra-sonic bath, followed by settling of suspended matter, 3 ml of the clear solution was analyzed for Mg and Al. Theory Al: 1.5 mmole, Found Al: 1.5 mmole. Theory Mg: 1.8 mmoles, Found Mg: 0.08 mmoles. Conclusion: Little effect of Aluminum alkoxide on solubility of Magnesium alkoxide in Freon TF, and therefore not a useful system for deacidification of books.

Basically, the gas expansion experiments were carried out in two types of apparatus. First, a small amount of the metal compound to be tested was dissolved in the desired solvent to an approximately 10% (by volume) level, and solubility tests run in a Jurgeson Gauge with the desired expander gas (see description below). If a reasonable expansion was evidenced on pressurization with the gas without precipitation of the compound, further testing was carried out on 3 inch by 3 inch sections of books (generally pre-dried before treatment) in a 3 liter steel pressure vessel.

The first type of test apparatus was a Jurgeson Gauge connected to a source of pressurized gas. The Jurgeson Gauge is essentially a steam boiler sight glass in which volume expansions of samples by test gas could be readily observed and measured. The sample, usually dissolved in a compatible solvent, is transferred under inert gas into the bottom of the gauge, its liquid level height measured (1,2,3 "bolts" on the front of the gauge) and the desired test gas pressured in slowly, measuring the volume expansion of the liquid samples as the pressure is increased incrementally. Generally, at some specific pressure and volume, the sample product becomes insoluble in the expanded solvent medium and precipitates. Then, as the pressure is slowly released from the system, the product redissolves. In this way, the solubility parameters for each test gas and sample solution combination can be measured and optimum book treatment conditions determined.

The three samples tested were given letter designations A, B, and C and were essentially free of solvent. Sample A was product from EXAMPLE I, Sample B was product from EXAMPLE IV (b), Sample C was product from EXAMPLE II, and Sample D was product from EXAMPLE III.

A test was run in the Jurgeson Gauge with a solution of Sample C in hexane (approximately 33 weight percent), pressurizing with $CO_2$ to about 900–1000 psi, less than a doubling of volume resulted before the inception of precipitation of product from solution. Exhaustion of gas with pressure reduction caused dissolution of the precipitated product. A 10 volume percent solution of Sample C in perchlorethylene, pressurized to 870 psi with $CO_2$, doubled in volume. The equivalent zinc and aluminum salts in perchlorethylene also showed this doubling effect.

Sample A solubilized well in Freon TF (20 weight percent) and a test was run with it and $CO_2$ in the Jurgeson Gauge. As the pressure was increased to Ca 500 psi, a thick viscous mass was formed in the gauge, which reverted back to a fluid solution on release of pressure. On running the same test with hexane in place of Freon TF, reversible precipitation occurred, but no thickening.

Sample B solubilized well in perchlorethylene, and a 10 volume percent solution was expanded with $CO_2$ to about 700 psi in the Jurgeson Gauge with an apparent doubling of the original solution volume before there was any indication of precipitation. In hexane, only about a 30% volume expansion occurred at about 600 psi before precipitation was noted.

Both pre-dried and undried 3 inch by 3 inch by 1 inch sections of an old book were treated with a $CO_2$ expanded (650 psi) 10 vol percent solution of Sample B in perchlorethylene (400 ml) in a 3 liter tubular pressure vessel for 10 minutes at room temperature. The books were positioned just above (¼ to ½ in.) the level of the liquid prior to pressurization with $CO_2$. The pressure was first increased to 500 psi and the liquid drained off, then the pressure bled off to zero. The vessel was once again pressured (to 1000 psi) with $CO_2$ for a few minutes and then the pressure released ($CO_2$ "rinse"). The undried book exhibited a white residue on the inside and outside of the covers and the pages close to the covers, with a "dusting" effect throughout. The pre-dried book showed no evidence of a white residue or any dusting. A page taken from the center of the pre-dried treated book was sprayed with a pH indicator solution and showed that an even distribution of deacidifying agent had been deposited thereon. ICP analysis for % Mg (as $MgCO_3$) of a page taken from the center of the book and cut into quarters gave the following results: Upper left quarter: 1.05; upper right quarter: 1.40; lower left quarter: 0.91; lower right quarter: 1.12. These results also indicated a fairly even deposition of deacidifying compound into the books. Cold water extraction (70 ml) of 1 gram of the pages taken from the center of the book (TAPPI T-509) gave a pH value of 8.3.

A rough comparison of the strength of the treated vs. untreated pages taken from the center of the book was made by determining the number of times the pages could be folded back and forth (fold axis parallel to binding) before breakage and separation. The untreated page showed only 3 folds to break, the treated, 21.

Tests were run in the Jurgeson Gauge using Compound A solubilized in hexane, but with ethane as the expanding gas.

With an 8.6% solution of A in hexane, a precipitate was noted at Ca 600 psi. This test was repeated enclosing a sheet of rolled up paper in the gauge, set above the initial liquid level in the gauge (before pressuring with ethane). After expansion of the liquid level onto the paper surface and precipitation of product, the paper strip showed striations on testing with pH paper indicating coalescence of the droplets of viscous product and uneven deposition onto the paper. The test was repeated at an ethane pressure below 500 psi which did not cause precipitation of the product, but which was sufficient to expand the solution volume to cover part of the test paper strip. After release of pressure, a dry paper was obtained. The immersed section of paper showed an even distribution of product onto the strip (pH indicator) giving the paper a satiny, smooth feel.

Another sample of A was dissolved in hexane (6 vol percent) and used to treat an old pre-dried book in the 3 liter pressure vessel using ethane as the expander gas (500 psi). The book was positioned above the liquid level before pressurization. Treatment time was approximately one minute. After drying, a treated page was cut into quarters and analyzed for % Mg (as $MgCO_3$) in each quarter. Results were as follows: Upper left quarter: 0.35; upper right quarter: 0.95; lower left quarter: 1.02; lower right quarter: 1.6. Even for only such a short treatment period, a significant deposition of magnesium had occurred in the book. Obviously, a longer treatment time is required for even deposition throughout the book.

The solution (approximately 5 vol/vol %) of EZMPG in Freon TF/PERC in EXAMPLE XIII was used to treat pre-dried 3 inch by 3 inch by 0.5 inch section of paperback novel by immersion in the circulating solution for a period of 20 minutes. After removal of the solution and drainage of any excess, the wet book was dried by stripping under vacuum (35°–40° C.) for a period of two hours. A pH indicator solution was sprayed onto a page of the book taken from the center and indicated an even distribution of deacidifying agent had been deposited. pH measurement by the TAPPI T-509 Cold Water Extraction test showed a pH of 8.0 (vs. 6.3 in an untreated book). Determination of evenness of deposition of deacidifier by ICP measurement of zinc (expressed as % ZnO) in a center page of the book cut into four equal squares gave the following results: Upper left corner: 1.43; upper right corner: 1.70; lower left corner: 1.48; lower right corner: 1.70. The untreated book showed no more than 0.005% ZnO in any square.

An 8 vol % solution of Compound B (EXAMPLE IV (b)) in Freon TF was prepared by adding 600 ml of solvent to 49.4 grams of B. The solution was used to treat books and pages from these books under a variety of conditions:

(a) Single page treatment: Triangular, freestanding forms were made up of three pages taken from a pre-dried book and stapled together. This form was placed in the treatment unit, treated for various times with the above TF solution of B, then dried by vacuum stripping. The dry pages were separated, and tested for (a) pH by Cold Water Extraction (TAPPI T-509), percent magnesium distribution in the quartered page by ICP, and number of folds to break (strength). The following Table shows the results obtained:

| Treatment Time min. | pH | Folds to Break | % Mg (ICP) in quartered page (as $MgCO_3$) | | | |
|---|---|---|---|---|---|---|
| | | | UL | UR | LL | LR |
| 2 | 8.6 | 4 | 2.13 | 2.03 | 2.31 | 2.28 |
| 5 | 8.7 | 16 | 2.31 | 2.35 | 2.52 | 2.59 |

-continued

| Treatment Time min. | pH | Folds to Break | % Mg (ICP) in quartered page (as MgCO$_3$) | | | |
|---|---|---|---|---|---|---|
| | | | UL | UR | LL | LR |
| 10 | 9.1 | 30 | 2.87 | 2.84 | 2.84 | 2.73 |

UL = upper left;
UR = upper right;
LL = lower left;
LR = lower right

The results indicated that longer treatment times improved the strength of the page as well as the evenness of distribution and amount of deposited de-acidifying agent in the page.

Further single page fold endurance tests were run comparing treated solution B in Freon TF with (a) Carbonated Butoxytriglycoxymagnesium-ω-methoxypolyethoxide (compound of EXAMPLE XII) in Freon TF (7.2 vol %), and (b) Carbonated Magnesium-bis-ω-methoxypolyethoxide (compound of EXAMPLE XI) in perchlorethylene (8.3 vol %).

Single 3 inch by 3 inch pages from an old book were stapled together as before and treated with the above solutions.

Results of the tests are as follows:

| Solution | No. of folds to break (Avg 3 tests) |
|---|---|
| B in TF | 29 |
| Comp'd of EX. XII in TF | 35 |
| Comp'd of EX. XI in PERC | 59 |
| Untreated | 7 |

These results indicate that longer poly(ethoxy) chains (7 ethoxy units in chain) impart greater strength to the pages than shorter chains (3 ethoxy units in the chain).

(b) Book Treatment: 3 inch by 3 inch by approximately 1 inch sections of an old book (both pre-dried and undried) were placed in the treatment vessel under inert gas (argon) and covered with the Freon TF solution of B used in (a) above. After 10 minutes, the treated solution was withdrawn, the books allowed to drain (15 minutes), and a vacuum applied (<1 mm) with exernal heating to about 35°–40° C. for 2 hours to dry the books. After returning the system to atmospheric pressure, the books were examined and tested as follows:

(i) Appearance: Undried book: white powdery patches on outside and inside of cover and throughout book. Pages have a powdery feel. Dried book: no white patches or powdery feel. Book appears unchanged from initial state.

(ii) pH (center page): undried book—8.6; dried book —8.7.

(iii) % Mg distribution (center page) as MgCO$_3$:

| Undried book: | UL - 2.14; UR - 1.79; LL - 1.96; LR - 1.75. |
|---|---|
| Dried book: | UL - 1.44; UR - 1.44; LL - 1.51; LR - 1.54. |

These results indicate that although deposition of deacidifier is greater in an undried book, as compared to a dried book, the deacidifier is not as evenly deposited, nor is it all deposited within the structure of the pages, i.e., some deacidifier is reacted with surface water and forms free (dusty) magnesium hydroxide, which is unacceptable. Pre-dried books were deacidified more evenly and completely and showed no obvious change in appearance before and after treatment.

TABLE I $(R^4O(CH_2CH(R^2)O)_nCH_2CH(R^2)O)_yM(OC(O)OCH(R^2)CH_2(OCH(R^3)CH_2)_mOR^3)_{2-y}(R^1OH)_x$
and
$(R^4O(CH_2CH(R^2)O)_nCH_2CH(R^2)OC(O)O)_yM(OCH(R^2)CH_2(OCH(R^3)CH_2)_mOR^3)_{2-y}(R^1OH)_x$

| M | R$^4$ | R$^2$ | R$^3$ | R$^1$ | m | n | y | x |
|---|---|---|---|---|---|---|---|---|
| Mg | C$_6$H$_{13}$ | H | C$_6$H$_{13}$ | — | 0 | 0 | 1.0 | 0 |
| Mg | C$_6$H$_{13}$ | H | C$_6$H$_{13}$ | — | 1.0 | 1.0 | 1.0 | 0 |
| Mg | C$_4$H$_9$ | H | C$_4$H$_9$ | — | 2.0 | 2.0 | 1.0 | 0 |
| Mg | C$_4$H$_9$ | CH$_3$ | C$_4$H$_9$ | — | 0 | 0 | 1.0 | 0 |
| Mg | C$_6$H$_{13}$ | H | CH$_3$ | — | 6.4 | 0 | 1.6 | 0 |
| Mg | C$_6$H$_{13}$ | H | CH$_3$ | — | 6.4 | 1.0 | 1.6 | 0 |
| Mg | C$_3$H$_7$ | CH$_3$ | C$_3$H$_7$ | — | 0 | 0 | 1.0 | 0 |
| Zn | C$_6$H$_{13}$ | H | C$_6$H$_{13}$ | — | 1.0 | 1.0 | 1.0 | 0 |
| Mg | CH$_3$ | H | CH$_3$ | — | 6.4 | 6.4 | 1.0 | 0 |
| Mg | C$_4$H$_9$ | H | CH$_3$ | — | 2.0 | 6.4 | 1.0 | 0 |
| Zn | CH$_3$ | H | CH$_3$ | — | 6.4 | 6.4 | 1.0 | 0 |
| Mg | CH$_3$ | H | CH$_3$ | C$_4$H$_9$(OCH$_2$CH$_2$)—CH$_2$CH$_2$— | 6.4 | 6.4 | 1.0 | 0.5 |

TABLE II $(R^4O)_yM(OC(O)OCH(R^2)CH_2-(-OCH(R^2)CH_2)_nOR^3)_{2-y}(R^1OH)_x$
and
$(R^4O(O)CO)_yM(OCH(R^2)CH_2-(-OCH(R^2)CH_2)_nOR^3)_{2-y}(R^1OH)_x$

| M | R$^4$ | R$^2$ | R$^3$ | R$^1$ | n | y | x |
|---|---|---|---|---|---|---|---|
| Mg | C$_2$H$_5$ | H | CH$_3$ | — | 6.4 | 1.0 | — |
| Mg | CH$_3$ | H | C$_2$H$_5$ | CH$_3$[1] | 2.0 | 1.0 | 1.0 |
| | | | | C$_4$H$_9$(OCH$_2$CH$_2$)$_2$—CH$_2$CH$_2$— | | | 0.5 |
| Mg | CH$_3$ | H | C$_4$H$_9$ | CH$_3$ | 2.0 | 1.0 | 1.0 |
| Mg | CH$_3$ | H | CH$_3$ | CH$_3$[1] | 2.0 | 1.0 | 1.0 |
| | | | | C$_4$H$_9$(OCH$_2$CH$_2$)$_2$—CH$_2$CH$_2$— | | | 1.0 |
| Mg | C$_2$H$_5$ | H | C$_4$H$_9$ | 4H$_9$(OCH$_2$CH$_2$)$_2$—CH$_2$CH$_2$— | 2.0 | 1.0 | 0.5 |
| Mg | C$_2$H$_5$ | H | CH$_3$ | 4H$_9$(OCH$_2$CH$_2$)$_2$—CH$_2$CH$_2$— | 6.4 | 1.0 | 0.5 |
| Mg | C$_2$H$_5$ | H | CH$_3$ | 4H$_9$(OCH$_2$CH$_2$)$_2$—CH$_2$CH$_2$— | 6.4 | 2.0 | 0.27 |

[1]R$^1$ is mixture of

We claim:

1. A process for deacidifying cellulosic materials comprising contacting the cellulosic material with a hydrocarbon or halocarbon solution or mixtures thereof containing an effective deacidifying amount of a composition selected from the group consisting of:

(A) a substituted metal alkoxide having the formula $$X_y M^a(OR)_{a-y}(R^1OH)_x$$

wherein:

(I) —OR is a group selected from 2-alkoxyalkoxy- and ω-alkoxypolyalkoxy- groups of the formula $$[-OCH(R^2)CH_2(OCH(R^2)CH_2)_n OR^3]$$

wherein $R^2$ is selected from H and —$CH_3$ and $R^3$ is selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20;

(II) X— is a group selected from
(a) 2-dialkylaminoalkoxy- and ω-dialkylaminopolyalkoxy groups of the formula $$[-OCH(R^2)CH_2(OCH(R^2)CH_2)_n NR_2^3]$$

wherein $R^2$ is selected from hydrogen and methyl, $R^3$ is selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20;

(b) a halogen selected from chlorine and bromine;
(c) an organic group —$R^4$ wherein $R^4$ is selected from the group consisting of alkyl groups containing 1 to 18 carbon atoms, cycloalkyl groups containing 3 to 18 carbon atoms and aryl, arylalkyl and alkylaryl groups containing 6 to 18 carbon atoms;
(d) an acyloxy group of the formula [—O(O)C$R^4$] wherein $R^4$ has the hereintobefore ascribed meaning;
(e) ω-alkoxypolyalkoxy- groups of the formula $$[-OCH(R^2)CH_2(OCH(R^2)CH_2)_n OR^3]$$

wherein $R^2$, $R^3$ and n have the herintobefore ascribed meanings;

(f) an alkoxy group —$OR^4$ wherein $R^4$ has the hereintobefore ascribed meanings;

(III) M is a metal selected from groups IIa and IIb of the Periodic Table and aluminum and mixtures thereof;

(IV) $R^1OH$ is a compound in which $R^1O$ is a group selected from (e) alkoxy groups of the formula $R^4O$ wherein $R^4$ has the hereintobefore ascribed meanings;

(f) 2-alkoxyalkoxy- and ω-alkoxypolyalkoxy- groups of the formula $$[-OCH(R^2)CH_2(OCH(R^2)CH_2)_n OR^3]$$

wherein $R^2$, $R^3$ and n have the hereintobefore ascribed meanings;

(g) 2-dialkylaminoalkoxy- and ω-dialkylaminopolyalkoxy groups of the formula $$[-OCH(R^2)CH_2(OCH(R^2)CH_2)_n NR_2^3]$$

(V) a is the valence of the metal M;
(VI) y has a value between zero and one; and
(VII) x has a value of zero to two;

(B) a carbonated substituted metal alkoxide having the formula $$X_y M^a(OR)_{a-y}(R^1OH)_x$$

in which either $X_y$ or —OR is carbonated wherein $R^1OH$, M, a, y and x have the hereintobefore ascribed meanings; and (I) —OR is a group selected from 2-alkoxyalkoxy- and ω-alkoxypolyalkoxy- groups of the formula $$[-OCH(R^2)CH_2(OCH(R^2)CH_2)_n OR^3]$$

wherein $R^2$ is selected from H and —$CH_3$ and selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20; and (II) X— is a group selected from
(a) 2-dialkylaminoalkoxy- and ω-dialkylaminopolyalkoxy groups of the formula $$[-OCH(R^2)CH_2(OCH(R^2)CH_2)_n NR_2^3]$$

wherein $R^2$ is selected from hydrogen and methyl, $R^3$ is selected from alkyl groups of 1 to 18 carbon atoms, cycloalkyl groups of 3 to 18 carbon atoms and aryl, arylalkyl and alkylaryl groups of 6 to 18 carbon atoms and n is a value of 1 to 20;

(b) an ω-alkoxypolyalkoxy- group of the formula $$[-OCH(R^2)CH_2(OCH(R^2)CH_2)_n OR^3]$$

wherein $R^2$, $R^3$ and n have the hereintobefore ascribed meanings; and, (c) an alkoxy group —$OR^4$ wherein $R^4$ has the hereintobefore ascribed meaning (C) and mixtures of (A) and (B).

2. The process of claim 1 wherein the solution is a 0.01 to 1 molar solution of the substituted metal alkoxide.

3. The process of claim 2 wherein the solution is a 0.02 to 0.5 molar solution of the substituted metal alkoxide.

4. The process of claim 2 wherein the solution is a 0.05 to 0.25 molar solution of the substituted metal alkoxide.

5. The process according to claim 1 wherein said cellulosic materials are contacted with halocarbon or hydrocarbon solutions or mixture thereof of substituted metal alkoxides and their carbonated derivatives under a pressure of up to 1000 psi.

6. The process of claim 1 wherein said substituted metal alkoxides are metal ω-alkoxypolyalkoxides of the type $$(R^4O(CH_2CH(R^2)O)_n CH_2CH(R^2)O)_y M^a(OCH(R^2)CH_2(OCH(R^2)CH_2)_m OR^3)_{a-y}(R'OH)_x$$

wherein $R^2$ is a hydrogen or methyl group and $R^3$ and $R^4$ are the same or different $C_1$ to $C_{18}$ alkyl groups, R' is a $C_1$ to $C_{18}$ alkyl, or ω-alkoxypolyalkoxyalkyl group, a is the valence of the metal, n and m are values from 1 to 20, and x is a value from zero to 2.

7. The process of claim 1 wherein said substituted metal alkoxides are alkylmetal 2-alkoxyalkoxy-, and ω-alkoxypolyalkoxides $R^1{}_yM[OCH(R)CH_2(OCH(R^2)CH_2)_n\text{-}OR^3]_{a-y}$, where $R^2$ is selected from hydrogen and a methyl group and $R^1$ and $R^3$ are the same or different $C_1$ to $C_{18}$ alkyl groups, a is the valence of the metal, y is a value from 0.1 to 1.0, and n is a value from 1 to 20.

8. The process of claim 1 wherein the substituted metal alkoxides are selected from the group of magnesium, zinc, aluminum alkoxides, and mixtures thereof.

9. The process of claim 1 wherein said carbonated derivatives of said substituted metal alkoxides are carbonated magnesium and zinc alkoxides and possess at least one carbonate group per metal atom.

10. The process of claim 1 wherein said carbonated substituted metal alkoxides are alkoxymagnesium-, alkoxyzinc-2-alkoxyalkoxides and magnesium, or zinc ω-alkoxypolyalkoxides of the formula

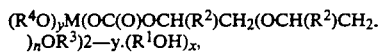

wherein M is selected from magnesium and zinc, $R^2$ is hydrogen or a methyl group, $R^3$ and $R^4$ are the same or different $C_1$ to $C_{18}$ alkyl groups, $R^1$ is a $C_1$ to $C_{18}$ alkyl, 2-alkoxyalkyl or ω-alkoxypolyalkoxyalkyl group, y is a value from 0.01 to 1, x is a value from zero to 2, and n is a value from 1 to 20.

11. The process according to claim 1 wherein said carbonated derivatives of said metal alkoxides are selected from magnesium bis-butoxytriglycolate, magnesium bis-ω-methoxypolyethoxide, zinc bis-butoxytriglycolate, zinc bis-ω-methoxypolyethoxide, magnesium bis-hexylcarbitolate, zinc bis-hexylcarbitolate, ethoxymagnesium ω-methoxypolyethoxide, methoxymagnesiumethoxytriglycolate, ethoxymagnesiumethoxytriglycolate, methoxymagnesiumbotoxytriglycolate and ethoxyzinc ω-methoxypolyethoxide, each member of the group complexed with from 0.01 to 0.5 molar equivalents of butoxytriglycol.

12. The process according to claim 1 wherein said cellulosic materials are contacted with normally liquid halocarbon and hydrocarbon solutions of metal alkoxides and their carbonated derivatives at atmospheric pressure, followed by removal of said solutions from said cellulosic materials.

13. The process according to claim 8 wherein said alkylmetalalkoxyalkoxides and alkylmetal ω-alkoxypolyalkoxides are selected from butylmagnesium ω-methoxypolyethoxide, ethylzinc ω-methoxypolyethoxide butylaluminum bis-ω-methoxypolyethoxide, and mixtures thereof.

14. The process according to claim 1 wherein the carbonated substituted metal alkoxides are selected from compounds having the formulae

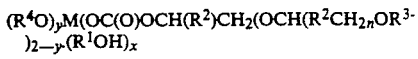

and

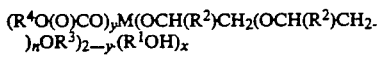

wherein M is selected from Mg, Zn, mixtures of Mg and Zn, $R^3$ and $R^4$ are $C_1$-$C_{18}$ alkyl groups, $R^2$ is hydrogen or methyl, $R^1$ is selected from $C_1$-$C_{18}$ alkyl groups which are the same as or different from $R^4$, $R^3O(CH_2CH_2O)_nCH_2CH_2$- and $R^4O(CH_2CH_2(R^2)O)_nCH_2CH(R^2)$ wherein $R^2$, $R^3$, $R^4$ and n have the herein ascribed meanings, y is a value from 0.01 to one, n is a value from 1 to 20 and x is a value from zero to two.

15. The process according to claim 1 wherein the carbonated substituted metal alkoxides are selected from compounds having the formulae

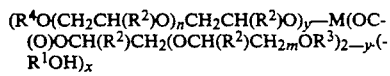

and

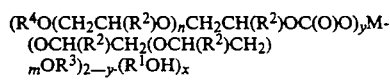

wherein M is selected from Mg, Zn, and mixtures thereof, $R^2$ is hydrogen or methyl, $R^4$ and $R^3$ are the same or different $C_1$-$C_{18}$ alkyl groups, $R^1$ is selected from $C_1$-$C_{18}$ alkyl groups which are the same as or different from $R^4$, $R^3O(CH_2CH_2O)_nCH_2CH_2$- and $R^4O(CH_2CH_2(R^2)O)_n$-$CH_2CH(R^2)$ wherein $R^2$, $R^3$, $R^4$ and n have the herein ascribed meanings, y is a value between 0.01, n and m are values from 1 to 20 and 1 and x is a value from between zero and two.

16. The process according to claim 15 wherein M is magnesium, n is 2, m is 2, $R^4$ is butyl, $R^3$ is butyl, $R^2$ is hydrogen and x is zero.

17. The process according to claim 15 wherein M is magnesium, n is 6.4, m is 2, $R^4$ is methyl, $R^3$ is butyl, $R^2$ is hydrogen and x is zero.

18. The process according to claim 12 wherein the hydrocarbon solvent is selected from the group consisting of pentane, hexane, heptane, benzene, toluene, cyclohexane, ethane, propane, butane, propylene and mixtures thereof.

19. The process according to claim 12 wherein the halocarbon is selected from the group consisting of 1,1,1-trichlorotrifluoroethane, symmetrical tetrachlorodifluoroethane, perchlorethylene, chloroform, methylchloroform, chlorotrifluoromethane, chlorodifluoroethane, 1,2-dichlorotetrafluoroethane and mixtures thereof.

* * * * *